(12) United States Patent
Miller et al.

(10) Patent No.: US 8,101,796 B2
(45) Date of Patent: Jan. 24, 2012

(54) PROCESS FOR THE PRODUCTION OF ACETIC ACID

(75) Inventors: Andrew John Miller, Kingston Upon Hull (GB); Marc John Payne, Henley-on-Thames (GB)

(73) Assignee: BP Chemicals Limited, Middlesex (GB)

( * ) Notice: Subject to any disclaimer, the term of this patent is extended or adjusted under 35 U.S.C. 154(b) by 367 days.

(21) Appl. No.: 12/223,103

(22) PCT Filed: Jan. 10, 2007

(86) PCT No.: PCT/GB2007/000054
§ 371 (c)(1),
(2), (4) Date: Jul. 22, 2008

(87) PCT Pub. No.: WO2007/085790
PCT Pub. Date: Aug. 2, 2007

(65) Prior Publication Data
US 2010/0228050 A1   Sep. 9, 2010

(30) Foreign Application Priority Data
Jan. 30, 2006  (GB) .................................. 0601865.9

(51) Int. Cl.
*C07C 51/12*   (2006.01)

(52) U.S. Cl. ........................................................ 562/519
(58) Field of Classification Search ........................ None
See application file for complete search history.

(56) References Cited

U.S. PATENT DOCUMENTS 5,696,284 A * 12/1997 Baker et al. .................... 560/232
7,692,040 B2 * 4/2010 Key et al. ....................... 562/519

FOREIGN PATENT DOCUMENTS

EP   0 749 948   12/1996
GB   2 327 420   1/1999

OTHER PUBLICATIONS

International Search Report for PCT/GB2007/000054 mailed Apr. 3, 2007.
Written Opinion for PCT/GB2007/000054 mailed Apr. 3, 2007.

* cited by examiner

*Primary Examiner* — Paul A Zucker
(74) *Attorney, Agent, or Firm* — Nixon & Vanderhye

(57) ABSTRACT

Process for producing acetic acid by carbonylating methanol and/or a reactive derivative thereof with carbon monoxide in at least one carbonylation reaction zone containing a liquid reaction composition containing an iridium carbonylation catalyst, methyl iodide co-catalyst, a finite concentration of water, acetic acid, methyl acetate. Indium and rhenium are present as promoters.

16 Claims, No Drawings

PROCESS FOR THE PRODUCTION OF ACETIC ACID

This application is the U.S. national phase of International Application No. PCT/GB2007/000054 filed 10 Jan. 2007 which designated the U.S. and claims priority to British Patent Application No. 0601865.9 filed 30 Jan. 2006, the entire contents of each of which are hereby incorporated by reference.

This invention relates to a process for the production of acetic acid and in particular to a process for the production of acetic acid by the carbonylation of methanol and/or a reactive derivative thereof in the presence of a promoted iridium catalyst.

The production of acetic acid by the carbonylation of methanol in the presence of an iridium catalyst and a promoter such as ruthenium is described, for example, in EP-A-0752406, EP-A-0849248, EP-A-0849249, and EP-A-1002785.

EP-A-0643034 describes a process for the carbonylation of methanol and/or a reactive derivative thereof in the presence of acetic acid, an iridium catalyst, methyl iodide, at least a finite concentration of water, methyl acetate and a promoter selected from ruthenium and osmium.

EP-A-0 749 948 describes a process for the carbonylation of an alkyl alcohol such as methanol and/or a reactive derivative thereof to produce the corresponding carboxylic acid and/or ester in the presence of an iridium catalyst, an alkyl halide, water and at least one promoter selected from cadmium, mercury, zinc, gallium, indium and tungsten, optionally with a co-promoter selected from ruthenium, osmium and rhenium.

In a carbonylation process employing an iridium catalyst promoted with ruthenium, it has been found that the higher the concentration of promoter, the greater the rate of reaction. However, it has also been found that under certain conditions precipitation of the catalyst system may occur.

Thus, there remains a need for an iridium-catalysed promoted carbonylation process in which the afore-mentioned disadvantages are mitigated.

The present invention solves the technical problem defined above by employing a non-ruthenium promoted iridium catalyst system wherein the catalyst system comprises iridium, indium and rhenium.

Accordingly, the present invention provides a process for the production of acetic, acid by carbonylating methanol and/or a reactive derivative thereof with carbon monoxide in at least one carbonylation reaction zone containing a liquid reaction composition comprising an iridium carbonylation catalyst, methyl iodide co-catalyst, a finite concentration of water, acetic acid, methyl acetate, and as promoters indium and rhenium.

It has now been found that by using an indium and rhenium promoted iridium catalyst system, the need for a ruthenium promoter is avoided whilst maintaining the carbonylation rate. In addition, there are environmental benefits associated with the present catalyst system as it has reduced toxicity compared to a ruthenium promoted iridium catalyst system.

In the process of the present invention, suitable reactive derivatives of methanol include methyl acetate, dimethyl ether and methyl iodide. A mixture of methanol and reactive derivatives thereof may be used as reactants in the process of the present invention. Water is required as co-reactant for ether or ester reactants. Preferably, methanol and/or methyl acetate are used as reactants.

At least some of the methanol and/or reactive derivative thereof will be converted to, and hence present as, methyl acetate in the liquid reaction composition by reaction with the carboxylic acid product or solvent. Preferably, the concentration of methyl acetate in the liquid reaction composition is in the range 1 to 70% by weight, more preferably 2 to 50% by weight, most preferably 3 to 35% by weight Water may be formed in situ in the liquid reaction compositions, for example, by the esterification reaction between methanol reactant and acetic acid product. Water may be introduced to the carbonylation reaction zone together with or separately from other components of the liquid reaction composition. Water may be separated from other components of the liquid reaction composition withdrawn from the reaction zone and may be recycled in controlled amounts to maintain the required concentration of water in the liquid reaction composition. Preferably, the concentration of water in the liquid reaction composition is in the range 0.1 to 20% by weight, more preferably 1 to 15% by weight, yet more preferably 1 to 10% by weight.

Preferably, the concentration of methyl iodide co-catalyst in the liquid reaction composition is in the range 1 to 20% by weight, preferably 2 to 16% by weight.

The iridium catalyst in the liquid reaction composition may comprise any iridium-containing compound which is soluble in the liquid reaction composition. The iridium catalyst may be added to the liquid reaction composition in any suitable form which dissolves in the liquid reaction composition or is convertible to a soluble form. Preferably the iridium may be used as a chloride free compound such as acetates which are soluble in one or more of the liquid reaction composition components, for example water and/or acetic acid and so may be added to the reaction as solutions therein. Examples of suitable iridium-containing compounds which may be added to the liquid reaction composition include $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_4I_2]^-H^+$, $[Ir(CO)_2Br_2]^-H^+$, $[Ir(CO)_2I_2]^-H^+$, $[Ir(CH_3)I_3(CO)_2]^-H^+$, $Ir_4(CO)_{12}$, $IrCl_3.4H_2O$, $IrBr_3.4H_2O$, $Ir_3(CO)_{12}$, iridium metal, $Ir_2O_3$, $IrO_2$, $Ir(acac)(CO)_2$, $Ir(acac)_3$, iridium acetate, $[Ir_3O(OAc)_6(H_2O)_3][OAc]$, and hexachloroiridic acid $H_2[IrCl_6]$, preferably, chloride-free complexes of iridium such as acetates, oxalates and acetoacetates.

Preferably, the concentration of the iridium catalyst in the liquid reaction composition is in the range 100 to 6000 ppm by weight of iridium.

The liquid reaction composition additionally comprises indium and rhenium promoters. The promoters may be added to the liquid reaction composition for the carbonylation reaction in any suitable form which dissolves in the liquid reaction composition or is convertible to soluble form.

Examples of suitable indium-containing compounds which may be used include indium acetylacetonate, indium acetate, $InCl_3$, $InBr_3$, $InI_3$, $InI$ and $In(OH)_3$.

Examples of suitable rhenium-containing compounds which may be used as sources of promoter include $Re_2(CO)_{10}$, $Re(CO)_5Cl$, $Re(CO)_5Br$, $Re(CO)_5I$, $ReCl_3.xH_2O$, $[Re(CO)_4I]_2$, $Re(CO)_4I_2]^-H^+$ and $ReCl_5.yH_2O$.

Preferably, each promoter is present in an effective amount up to the limit of its solubility in the liquid reaction composition and/or any liquid process streams recycled to the carbonylation reactor from the acetic acid recovery stage. Each promoter is suitably present in the liquid reaction compositions at a molar ratio of promoter to iridium of [greater than 0 to 15]:1 such as in the range [2 to 10]:1, for example [2 to 5]:1. Each promoter is suitably present in the liquid reaction composition in a concentration less than 8000 ppm.

Suitably, the molar ratio of iridium:indium:rhenium may be in the range 1:[greater than 0 to 15]:[greater than 0 to 15], such as 1:[2 to 10]:[2 to 10], for example 1:[2 to 5]:[2 to 5].

Preferably, the iridium, indium and rhenium containing compounds are free of impurities which provide or generate in situ ionic iodides which may inhibit the reaction, for example, alkali or alkaline earth metal or other metal salts.

Ionic contaminants such as, for example, (a) corrosion metals, particularly nickel, iron and chromium and (b) phosphines or nitrogen containing compounds or ligands which may quaternise in situ; should be kept to a minimum in the liquid reaction composition as these will have an adverse effect on the reaction by generating I⁻ in the liquid reaction composition which has an adverse effect on the reaction rate. Some corrosion metal contaminants such as for example molybdenum have been found to be less susceptible to the generation of I⁻. Corrosion metals which have an adverse affect on the reaction rate may be minimised by using suitable corrosion resistant materials of construction. Similarly, contaminants such as alkali metal iodides, for example lithium iodide, should be kept to a minimum. Corrosion Metal and other ionic impurities may be reduced by the use of a suitable ion exchange resin bed to treat the reaction composition, or preferably a catalyst recycle stream. Preferably, ionic contaminants are kept below a concentration at which they would generate 500 ppm I⁻, preferably less than 250 ppm I⁻ in the liquid reaction composition.

The carbon monoxide reactant for the carbonylation reaction may be essentially pure or may contain inert impurities such as carbon dioxide, methane, nitrogen, noble gases, water and $C_1$ to $C_4$ paraffinic hydrocarbons. The presence of hydrogen in the carbon monoxide and generated in situ by the water gas shift reaction is preferably kept low, for example, less than 1 bar partial pressure, as its presence may result in the formation of hydrogenation products. The partial pressure of carbon monoxide is suitably in the range 1 to 70 bar, preferably 1 to 35 bar and more preferably 1 to 15 bar.

The total pressure of the carbonylation reaction is suitably in the range 1.0 to 20.0 Mpag (10 to 200 barg), preferably 1.0 to 10.0 Mpag (10 to 100 barg), more preferably 1.5 to 5.0 Mpag (15 to 50 barg). The carbonylation reaction temperature is preferably in the range 150 to 220° C.

The process of the present invention may be performed as a batch or a continuous process, preferably as a continuous process.

The acetic acid product may be removed from the carbonylation reaction zone by withdrawing liquid reaction composition and separating the acetic acid product by one or more flash and/or fractional distillation stages from the other components of the liquid reaction composition such as iridium catalyst, indium and rhenium promoters, methyl iodide, water and unconsumed reactants which may be recycled to the carbonylation reaction zone to maintain their concentrations in the liquid reaction composition.

The process of the present invention may be carried out in a single reaction zone or it may be carried out in two or more reaction zones. Where two or more reaction zones are employed, the liquid reaction composition and reaction conditions in each reaction zone may be the same or different.

The invention will now be illustrated by way of example only by reference to the following examples.

General Reaction Method

All experiments were performed in a 300 cm³ zirconium autoclave equipped with a stirrer and a liquid injection facility. The autoclave was pressure tested to a minimum of 30 barg with nitrogen and then flushed three times with carbon monoxide up to 3 barg. A charge consisting of methyl acetate, acetic acid, methyl iodide, water and promoter was placed in the autoclave and a small amount of carbon monoxide was placed over the charge. A ballast vessel was charged with an overpressure of carbon monoxide.

The autoclave was heated with stirring-(1500 rpm) to 190° C. The catalyst injection system was primed with an iridium acetate solution (approx 5% iridium, 26% water, 62.7% acetic acid) and acetic acid and injected with carbon monoxide to bring the autoclave pressure to 28 barg The reaction rate was monitored by a drop in the carbon monoxide pressure from the ballast vessel. The autoclave was maintained at a constant temperature of 190° C. and pressure of 28 barg throughout the reaction. After uptake of carbon monoxide from the ballast vessel had ceased, the autoclave was isolated from the gas supply and cooled. After cooling, a gas analysis sample was taken and the autoclave vented. The liquid components were discharged, and analysed for liquid by-products by known established gas chromatography methods. Detected components were quantified by integration of the component peaks relative to an external standard and expressed as parts per million (ppm) by weight. The major product obtained in each carbonylation experiment was acetic acid.

The rate of gas uptake at a certain point in a reaction run was used to calculate the carbonylation rate, as number of moles of reactant consumed per liter of cold degassed reactor composition per hour (mol/l/h) at a particular reactor composition (total reactor composition based on a cold degassed volume)

The methyl acetate concentration was calculated during the course of the reaction from the starting composition, assuming that one mole of methyl acetate was consumed for every mole of carbon monoxide that was consumed. No allowance was made for organic components in the autoclave headspace. The gaseous by-products were analysed by gas chromatography and results calculated in terms of % selectivity based on methyl acetate consumption for methane and CO consumption for $CO_2$.

EXAMPLES

Experiment A

A baseline experiment was performed with the autoclave charged with an iridium acetate solution and a ruthenium acetate solution (5% ruthenium, 18% water and 72% acetic acid). The amounts of the components charged to the autoclave are given in Table 1 below. The rate of reaction at a calculated reaction composition of 12% methyl acetate is shown in Table 2.

Experiment B

Experiment A was repeated except that the autoclave was charged with indium acetate solution instead of a ruthenium solution. The amounts charged to the autoclave are given in Table 1 and the results of the experiment are given in Table 2.

Experiment C

Experiment A was repeated except that the autoclave was charged with dirhenium decocarbonyl solution instead of a ruthenium solution. The amounts charged to the autoclave are given in Table 1 and the results of the experiment are given in Table 2.

Examples 1 and 2

Experiment A was repeated except that the autoclave was charged with indium acetate solution and dirhenium decocarbonyl solution instead of a ruthenium solution.

The amounts charged to the autoclave are given in Table 1 and the results of the experiment are given in Table 2.

The results in Table 2 show that a combination of indium and rhenium promote an iridium catalysed methanol carbonylation process with no detriment to the carbonylation rate.

TABLE 1

Autoclave Charges

| Experiment | Catalyst System (molar ratio) | Ir acetate (g) | Ru acetate (g) | In acetate (g) | Dirhenium decocarbonyl (g) | Methyl Acetate (g) | Water (g) | Methyl iodide (g) | Acetic Acid (g) |
|---|---|---|---|---|---|---|---|---|---|
| Experiment A | Ir/Ru (1:2) | 6.6 | 6.87 | 0 | 0 | 48.0 | 12.64 | 13.33 | 65.28 |
| Experiment B | Ir/In (1:2) | 6.6 | 0 | 1.02 | 0 | 48.0 | 13.8 | 14.81 | 64.7 |
| Experiment C | Ir/Re (1:2) | 6.6 | 0 | 0 | 1.14 | 48.0 | 13.8 | 15.78 | 64.7 |
| Example 1 | Ir/In/Re (1:3:3) | 6.6 | 0 | 1.53 | 1.70 | 48.0 | 13.8 | 19.21 | 60.65 |
| Example 2 | Ir/In/Re (1:2:2) | 6.6 | 0 | 1.01 | 1.14 | 48.0 | 13.8 | 17.77 | 52.7 |

TABLE 2

Rate and By-product data

| Experiment | Rate at 12 wt % MeOAc mol/l/h | Propionic Acid (ppm) | Methane Selectivity % | $CO_2$ Selectivity % |
|---|---|---|---|---|
| Experiment A | 19 | 400 | 1.5 | 1.0 |
| Experiment B | 14.8 | 640 | 1.5 | 2.4 |
| Experiment C | 10.0 | 420 | 0.6 | 1.3 |
| Example 1 | 19 | 550 | 2.3 | 1.0 |
| Example 2 | 18.5 | 560 | 1.0 | 1.8 |

The invention claimed is:

1. A process for the production of acetic acid comprising carbonylating methanol and/or a reactive derivative thereof with carbon monoxide in at least one carbonylation reaction zone containing a liquid reaction composition comprising an iridium carbonylation catalyst, methyl iodide co-catalyst, a finite concentration of water, acetic acid, methyl acetate and as promoters indium and rhenium.

2. A process according to claim 1 wherein the indium promoter and rhenium promoter are each present in the liquid reaction composition at a molar ratio of promoter to iridium of [[greater than 0] to 15]:1.

3. A process according to claim 1 wherein the molar ratio of iridium:indium is in the range 1:[2 to 10] and the molar ratio of iridium:rhenium in the range 1:[2 to 10].

4. A process according to claim 3 wherein the molar ratio of iridium:indium is in the range 1:[2 to 5] and the molar ratio of iridium:rhenium in the range 1:[2 to 5].

5. A process according to claim 1 wherein the concentration of each promoter in the liquid reaction composition is less than 8000 ppm.

6. A process according to claim 1 wherein the concentration of iridium in the liquid reaction composition is in the range 100 to 6000 ppm.

7. A process according to claim 1 wherein water is present in the liquid reaction composition at a concentration in the range 0.1 to 20% by weight.

8. A process according to claim 7 where the water concentration is in the range 1 to 15% by weight.

9. A process according to claim 8 wherein the water concentration is in the range 1 to 10% by weight.

10. A process according to claim 1 wherein the methyl acetate is present in the liquid reaction composition at a concentration in the range 1 to 70% by weight.

11. A process according to claim 1 wherein the methyl iodide is present in the liquid reaction composition at a concentration in the range 1 to 20% by weight.

12. A process according to claim 1 wherein the carbonylation reaction is carried out at a total pressure in the range 1 to 20 MPaG.

13. A process according to claim 1 wherein the carbonylation reaction is carried out at a temperature in the range 150 to 220° C.

14. A process according to claim 1 wherein the carbonylation reaction is carried out in a single carbonylation reaction zone.

15. A process according to claim 1 wherein the carbonylation reaction is carried out in at least two carbonylation reaction zones.

16. A process according to claim 1 wherein the process is carried out as a continuous process.

* * * * *